United States Patent [19]

Csillag

[11] Patent Number: 4,810,447
[45] Date of Patent: Mar. 7, 1989

[54] SYSTEM FOR IMPROVED FLAW DETECTION IN POLYCRYSTALLINE DIAMOND

[75] Inventor: Frank J. Csillag, Westerville, Ohio

[73] Assignee: General Electric Company, Worthington, Ohio

[21] Appl. No.: 697,668

[22] Filed: Feb. 4, 1985

[51] Int. Cl.$^4$ ............................................. B29C 67/00
[52] U.S. Cl. ..................................... 264/125; 51/307; 51/309
[58] Field of Search .................... 264/125, 60; 51/307, 51/309

[56] References Cited

U.S. PATENT DOCUMENTS

| | | | |
|---|---|---|---|
| 2,796,706 | 6/1957 | Anderson | 51/206 |
| 2,818,850 | 1/1958 | Schwarzkopf | 125/15 |
| 3,831,428 | 8/1974 | Wentorf | 72/467 |
| 3,913,280 | 10/1975 | Hall | 51/307 |
| 4,129,052 | 12/1978 | Bieberich | 76/107 |
| 4,144,739 | 3/1979 | Corbin | 72/467 |
| 4,268,276 | 5/1981 | Bovenkerk | 51/295 |
| 4,370,149 | 1/1983 | Hara et al. | 51/309 |

FOREIGN PATENT DOCUMENTS 756730 4/1977 South Africa .
817930 2/1983 South Africa .

OTHER PUBLICATIONS

Ortner (Editor), "On the Properties of Fine Grain Sintered Diamond Bodies", *Proceedings of the 10th Plansee–Seminar, Metal Work Reutte, Austria*, vol. 2, pp. 581–589.
Taylor, "Diamond–Impregnated Carboloy", General Electric Review, vol. 67, No. 2, Feb. 1934.

*Primary Examiner*—James Derrington
*Attorney, Agent, or Firm*—Gary L. Loser; Robert R. Schroeder

[57] ABSTRACT

Disclosed is an improvement enabling a more reliable detection of flaws in polycrystalline diamond compacts by x-ray imaging and especially for compacts used for wire drawing dies. In an embodiment, wire die compacts are prepared having a polycrystalline diamond core disposed within a metal carbide annulus. In the core are uniformly dispersed less than five (5) percent by weight particles such as tungsten carbide which initially have an average particle size substantially less than the diamond particles used to form the polycrystalline mass.

10 Claims, 1 Drawing Sheet

SYSTEM FOR IMPROVED FLAW DETECTION IN POLYCRYSTALLINE DIAMOND

BACKGROUND ON THE INVENTION

The present invention relates to methods for producing polycrystalline diamond compacts made by high pressure/high temperature processes (HP/HT), and more particularly to a method whereby the ability to reliably detect flaws in polycrystalline diamond masses when using x-ray imaging techniques is improved. This invention has special application with respect to supported polycrystalline diamond wire die compacts.

A polycrystalline diamond wire die compact comprises a mass of polycrystalline diamond which mass is then pierced to enable wire to be drawn through it. The polycrystalline diamond mass comprises diamond particles bonded one to another to form an integral, tough, coherent, high strength body typically having a diamond concentration of at least seventy (70) volume percent. The formation of extensive diamond-to-diamond bonds between the particles is achieved using a sintering aid such as cobalt. While such diamond masses can be directly attached to a holding fixture, they are typically and conveniently produced integral with a surrounding annular support of metal bonded carbide such as cobalt cemented tungsten carbide. Representative conventional polycrystalline diamond wire die compacts are disclosed, for example, in U.S. Pat. Nos. 3,831,428, 4,129,052, and 4,144, 739.

While such diamond compacts may be produced from a range of diamond particle sizes, the ease of finishing diamond wire dies that have been sintered from fine grain diamond, e.g., less than about 10 microns, and the improved surface finish of wires that have been drawn through such dies make fine grained diamond compacts especially desirable in the marketplace. This is noted, for example, in U.S. Pat. No. 4,370,149.

Although polycrystalline wire die compacts offer a number of advantages, their production has been difficult due to unacceptable incidents of flaws in the diamond cores. The incidence of flaws during fabrication tends to increase with the size of the polycrystalline mass and as the diamond feed size decreases. It has been suggested that the addition of particles of other materials designed to inhibit excessive regrowth during the formation of diamond-to-diamond bonds can account for some improvement in producing flaw-free diamond masses. Hara et al., "On the Properties of Fine Grain Sintered Diamond Bodies," *Proceedings of the 10th Plansee-Seminar,* Hugo M. Ortner, Editor, Metal Work Plansee, Reutte, Austria, Vol. 2, pp. 581–589(1981). Another technique proposed to improve the diamond compact portion of the wire drawing dies is the use of additives, such as boron, tungsten carbide, and the like, as set forth in U.S. Pat. Nos. 3.913,280, 4,268,276, 4,370,149, and South African Application No. 756730.

Yet another approach is the so-called "axial infiltration" technique as disclosed in commonly-assigned application of Cho, U.S. Ser. No. 313,119, filed Oct. 20, 1981, now U.S. Pat. No. 4,534,934. This technique involves the placement of a source of a catalyst/solvent sintering aid on one axial end of a diamond mass to be sintered followed by application HP/HT. While such improvements are helpful, it remains vital to accurately detect those flaws which do occur.

Flaws that develop in the production of polycrystalline diamond compacts which are of particular concern include poorly or non-uniformly bonded zones characterized by a lower hardness than non-flawed areas. They can result from a high or low concentration of sintering aid which can lead to a lesser amount of diamond-to-diamond bonding. Flawed zones can exhibit a different coloration from the non-flawed areas or a different texture. Flaws near the surface of polycrystalline diamond compacts are often detectable visually and can normally be remedied by lapping or other mechanical means. Flaws within a polycrystalline mass are more difficult to detect. Moreover, since the interior of a wire die performs the wire drawing operation, internal flaws are especially critical in a polycrystalline diamond wire die compact. Consequently, methods for accurately and reliably detecting or sensing such flaws or poorly bonded zones is quite important to both the manufacturer of the polycrystalline diamond wire drawings dies as well as for the users of such dies.

Present day practice involves the use of x-ray radiographs of the diamond wire die compacts in order to detect internal flaws. It is an object of the present invention to provide a compact which will enable an increase in the ability to reliably detect flaws using such conventional x-ray techniques.

BROAD STATEMENT OF THE INVENTION

The present invention is directed to polycrystalline diamond compact and a method for producing the same, which compact enables improved flaw detectability using conventional x-ray radiography means. The compact is formed by placing a quantity of diamond particles in the presence of less than thirty (30) volume percent sintering aid material such as cobalt under HP/HT conditions sufficient to form a polycrystalline mass. The improvement comprises uniformly dispersing within the diamond particles prior to said HP/HT conditions a controlled amount of an element which has a substantially higher atomic number than that of the sintering aid. For example, when cobalt or nickel is used as a sintering aid, zirconium or a higher atomic weight element such as tantalum or tungsten is advantageously added. Tungsten is preferred because it has a high atomic weight and it is a carbide former resulting in a more stable final structure. An element such as tungsten may be added as a metal, or it may be added as a compound such as a carbide or a cemented carbide.

The particle size of the heavy element material should be less than and preferably significantly less than the size of the diamond particles so as not to unnecessarily restrict the flow of molten sintering aid material around the diamond particles during a HP/HT process. In the case of carbide powder, for example, the particle size will advantageously be less than about three (3) microns in average particle size. The amount of high atomic weight element should be sufficient to approximate, and preferably be slightly greater than that needed to reach the solubility limit of that element in the sintering aid material in the final product. In the case of a metal carbide such as tungsten carbide in a cobalt sintering aid, an amount of metal carbide powder equal to less than 5% by weight of the diamond particles is preferred. Typically, the metal carbide powder is present in a proportion ranging from between about one (1) and five (5) weight per cent.

Advantages of the present invention include improving the reliability of x-ray radiographic imaging of polycrystalline diamond compacts to detect flaws within the polycrystalline diamond mass which flaws are deleterious to the performance otherwise achievable by the polycrystalline compacts. Another advantage is that such improved flaw detection technique does not adversely affect the performance of the polycrystalline compacts. A further advantage is that the method of the present invention can be implemented readily and integrated into existing commercial processes and plants which prepare polycrystalline compacts. These and other advantages will be readily apparent to those skilled in the art based upon the disclosure contained herein.

Figure 2:
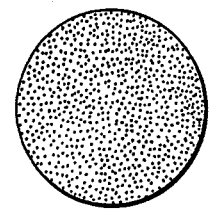
FIG. 2 represents an x-ray radiograph of polycrystalline diamond wire die compact prepared in accordance with the present invention.

The drawings will be described in greater detail in connection with the following Detailed Description of the Invention.

DETAILED DESCRIPTION OF THE INVENTION

The present invention has applicability to the manufacture of polycrystalline diamond masses in general, but has particular applicability to those configured for use as wire dies. Such compacts are typically x-ray imaged through the diamond mass without any intervening layer of other material that might otherwise detract from the ability to detect flaws by interpretation of resulting images. Similarly, although such wire die compacts may include those configured as an unsupported polycrystalline mass, this invention has particular utility with respect to supported wire die compacts formed with an integral annulus of a material such as cemented tungsten carbide. As used herein, a polycrystalline diamond mass is one exhibiting extensive diamond-to-diamond bonding formed under HP/HT conditions.

Methods of producing supported polycrystalline wire die compacts are well known as are the HP/HT conditions and sintering aid materials needed to achieve diamond-to-diamond bonding. For example, see U.S. Pat. No. 3,831,428. In a typical process diamond particles are placed in a cobalt cemented tungsten carbide annulus, and this assembly is then subjected to appropriate HP/HT conditions. Sintering aid material is made available to the diamond in the form of liquid cobalt flowing from the annular support during the process. Additional sintering aid material may initially be present in the form of particles dispersed in the diamond or as a supplemental layer adjacent the diamond. The polycrystalline diamond core will retain the infiltrated sintering aid material as well as any additives utilized in the process, including, for example, copper, boron, tantalum, tungsten, molybdenum, niobium, and the like. Additionally, infiltration of other metals from carbide annulus into the diamond core occurs. Thus besides some cobalt or other catalyst typically contained in the carbide annulus, tungsten can also infiltrate from the carbide annulus into the polycrystalline diamond core. Tungsten will be used as the example metal since tungsten carbide annuli find the most use in polycrystalline wire die compacts. It should be understood, however, that other metals of metal carbides (e.g., tantalum, or the like) similarly could infiltrate into the polycrystalline diamond core during the HP/HT process. The same is true of additive metals which may be contained within the carbide annulus (e.g. molybdenum). Infiltrated tungsten or a like metal from the carbide annulus causes particular problems in x-ray radiographs since it is a relatively high atomic weight element as compared to carbon. The problem occurs since the radiographic image is sensitive to densities and density gradients, thus making concentration gradients of relatively heavier elements more pronounced in the radiograph image.

More specifically, a widely-used and commercially-accepted method for sensing interior flaws or poorly-bonded zones in a polycrystalline diamond wire die compact involves the interpretation of x-ray images. X-ray radiographic imaging of polycrystalline diamond wire dies provides a visible indicia of the densities of the various materials contained within the dies. For example, an x-ray radiographic image of a homogeneous polycrystalline diamond compact will have a uniform color and intensity when sufficient x-rays have passed through the compact to darken but not saturate the film. Thus when the x-ray radiographic image of the polycrystalline diamond core of a wire die appears uniform in color and intensity, it is an indication that the core is flaw-free. However, x-ray imaging is acutely sensitive to variations in density and visually expresses such density gradient by color and intensity of color, ranging from clear through various shades of gray to black. The x-ray image is not typically used to determine concentrations of ingredients in a polycrystalline diamond mass, but rather variations in density. For example, detectable variations in metal concentrations in the polycrystalline diamond core could range in concentration between adjacent areas from $10^{-4}$ weight percent in one to $10^{-2}$ weight percent in the other, particularly when a dense material such as tungsten is involved. While the concentration of the metal is quite low in both areas, the relative order of magnitude of such impurity metals readily is perceptible on an x-ray radiographic image. The problem facing the artisan interpreting the radiographic image is to distinguish between unacceptable flaws and acceptable variations in metal or other chemical concentration when both occurrences appear substantially the same on the x-ray radiographic image.

In a conventional process for producing a polycrystalline wire die in which the sintering aid material infiltrates radially from a surrounding annulus, tungsten appears to be carried out of the annulus by the cobalt or other sintering aid during the process. Such carried tungsten is typically in an equilibrium concentration in solution as tungsten carbide in the cobalt and is normally carried into the core uniformly throughout the interface of the diamond core and annulus. However, the problem is exacerbated when a supplemental supply of sintering aid is provided for the diamond core such as where an axial infiltration process is used as described in patent application U.S. Ser. No. 313,119, now U.S. Pat. No. 4,534,934, cited above. In this case, little or no cobalt from the annulus may infiltrate into the polycrystalline diamond core. As a result tungsten migration into the core tends to be very non-uniform along the core-annulus interface. Thus, a significant concentration gradient of tungsten can appear throughout the volume of the diamond core. As noted above, such concentration gradient is expressed in an x-ray radiograph image in a manner which may be indistinguishable from that of a flaw such as an unbonded zone or a crack.

A fundamental object of the present invention is to create a more homogeneous chemical system in the polycrystalline diamond core and the metal carbide annulus so that the annulus chemistry does not significantly alter the chemistry of the polycrystalline diamond core. Such result would translate into the x-ray radiographic imaging process being more sensitive to the presence of undesirable flaws with the incidence of false positive readings being dramatically reduced. This object is achieved in the present invention through a reduction in the radiographic image contrast of the elements in the sintering aid relative to one another without significantly reducing the contrast to the diamond material. Such homogeneity is created by uniformly dispersing particles containing a heavy element material such as particles of tungsten carbide or cemented tungsten carbide in the diamond particles prior to the HP/HT axial sweep-through process. The amount of additive tungsten carbide typically should be less than about 5 weight percent (by weight of the diamond particles) and typically such concentration ranges from about 3 to 5 weight percent. Of course, the concentration and type of heavy metal additive should be correlated to the particular grade and elemental composition of cemented metal carbide used. Ideally, the composition of the metal phase of the sintered diamond core should be in close correspondence in atomic weight with that of the cemented metal carbide used as an annulus for example. The amount of heavy element additive should be adjusted to approximate, and preferably slightly exceed the solubility limit of that element in the sintering aid phase. As indicated, in the case of a tungsten carbide powder in a cobalt sintering aid phase, an addition of less than five percent (5%) by weight of the carbide powder has been found adequate, and between three percent (3%) and five percent (5%) is preferable.

With the uniform dispersal of the additive tungsten carbide in the polycrystalline diamond core, non-uniform infiltration of tungsten from the annulus will create less of a concentration gradient within the diamond core. Such diminished concentration gradient translates into a more uniform x-ray radiographic image.

Figure 1:
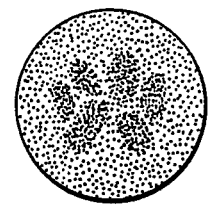
FIG. 1 represents an x-ray radiograph of a conventional polycrystalline wire die compact.

Such enhanced accuracy and reliability in detecting flaws in polycrystalline diamond cores or polycrystalline diamond wire die compacts can be seen readily by reference to FIGS. 1 and 2. FIG. 1 is a depiction of an x-ray radiographic image of a polycrystalline diamond wire die compact made by the axial infiltration process of application U.S. Ser. No. 313,119, now U.S. Pat. No. 4,534,934, as cited above. It will be observed that the sintered polycrystalline diamond core exhibits areas of different color and intensity which indicates that a density gradient exists. However, from such radiographic image, it cannot be truly ascertained whether flaws in the polycrystalline diamond core actually exist or whether an acceptable concentration gradient of tungsten or other hand metal is present. The core depicted in FIG. 1 was subjected to further analysis (e.g. by sectioning the core and examining the interior) and failed to exhibit any objectionable flaws. This suggests that the non-uniform radiographic image was the result of density differentials caused by tungsten metal in the core, which tungsten metal probably was infiltrated into the core from its respective tungsten carbide annulus.

The polycrystalline diamond wire die depicted in FIG. 2 was made by the same axial infiltration process under substantially identical conditions as the dies depicted in FIG. 1. The only difference between the two dies is that the polycrystalline diamonds used to make the diamond core of the die in FIG. 2 contained four weight percent (1 volume percent) of cemented tungsten carbide powder (average particle size of less than 3 microns). In this case the carbide powder was added by milling diamond particles for twenty-four (24) hours in a cemented tungsten carbide container using cemented tungsten carbide balls.

It will be observed that the diamond core of the die in FIG. 2 has a much more uniform color and intensity; thus enabling a much needed improvement in the ability of the x-ray radiographic process to reliably detect flaws in the diamond core. Several cores produced in this manner were later sectioned and were found to be free of flaws.

While most carbide powders for use in the present invention will typically be less than 3 microns in average particle size, such carbide powders can range up to as large as about 10 microns and should be small compared to the diamond particles so as not to disrupt the flow of sintering aid. The carbide powder or cemented carbide powder can be milled with the diamond in a carbide or similar mill to uniformly coat the diamond particles therewith. Alternatively, additions of metal carbide or cemented metal carbide powder can be made by simply mixing diamond particles with the required quantity of such additive carbide powder. The presence of the carbide powder does not appear to detract from the performance of the dies and, in fact, is thought to enhance the axial infiltration process by improving the ability to flow into the diamond and by minimizing volume changes which occur in the diamond core during the HP/HT process. It will be appreciated that the additive metal preferably will be of the same composition as the metal of the metal carbide annulus, though any suitable carbide or cemented carbide may be utilized. Cemented tungsten carbide powders preferably will contain cobalt, though nickel, iron, or other metal, especially a diamond sintering aid metal, may be used in accordance with the present invention. Preferably, the additive carbide powder will be tungsten carbide or cobalt cemented tungsten carbide powder. As noted above, metal particles may also be employed in this invention. In addition to tungsten, tantalum and zirconium already mentioned, other elements of atomic number greater than zirconium and which are carbide formers may also be used in the present invention. These include niobium, molybdenum and uranium.

With reference to the axial infiltration process, as disclosed in U.S. Ser. No. 313,119, now U.S. Pat. No. 4,534,934 cited above, a source of sintering aid, optionally along with a refractory metal, may be placed at or end of the carbide annulus bearing the diamond particles followed by practice of a conventional HP/HT process. In order to enhance the removal of surface absorbed species including oxygen and water, as well as other impurities which may be contained in the diamond particles, a process utilizing a pre-sweep with a metal, such as copper, which melts at a lower temperature than the sintering aid of choice, may be employed as disclosed in commonly-assigned application of Gigl et al, U.S. Ser. No. 536,221 filed Sept. 23, 1983, now U.S. Pat. No. 4,518,659. Such pre-sweep enhances the pushing of impurities from the diamond consolidation zone for minimizing non-diamond-to-diamond bonding zones in the compact.

In this application, all percentages and proportions are by weight and all units are in the metric system, unless otherwise expressly indicated. Also, all references cited herein are incorporated expressly herein by reference.

I claim:

1. In a process for producing a polycrystalline diamond mass wherein a quantity of diamond particles is placed in contact with a sintering aid material and a source of infiltrable material under sintering conditions of temperature and pressure and for a period of time adequate to form said polycrystalline mass, said source of infiltrable material resulting in a non-uniform visible image by X-ray of said polycrystalline mass, the improvement for enabling reliable flaw detection in said polycrystalline mass, which comprises uniformly dispersing metal particles comprising a metal which has a higher atomic number than that of said sintering aid material, is a carbide former, and has an atomic number greater than 39, in said diamond particles in an amount less than five percent (5%) by weight of the diamond particles prior to placing the diamond particles under said sintering conditions.

2. The process of claim 1 wherein the metal particles are of an average particle size less than the average particle size of said diamond particles.

3. The process of claim 2 wherein the metal particles are less than ten (10) microns in average size.

4. The process of claim 3 wherein the metal particles are less than three (3) microns in average size.

5. The process of claim 1 wherein metal particles are dispersed in said diamond particles in an amount of between three percent (3%) and five percent (5%) by weight of the quantity of diamond particles.

6. The process of claim 1 wherein the metal of said metal particles is selected from the group consisting of zirconium, tungsten, tantalum, niobium, molybdenum, uranium and mixtures and alloys thereof.

7. The process of claim 1 wherein the metal of said metal particles is selected from zirconium, tungsten, tantalum and mixtures and alloys thereof.

8. The process of claim 1 wherein the metal of said metal particles is tungsten.

9. The process of claim 1 wherein said metal particles comprise tungsten carbide particles.

10. The process of claim 1 wherein said metal particles comprise cemented metal carbide particles.

* * * * *